United States Patent
Juvinall et al.

[11] Patent Number: 5,200,801
[45] Date of Patent: Apr. 6, 1993

[54] INSPECTION OF CONTAINER FINISH

[75] Inventors: John W. Juvinall, Ottawa Lake; Robert D. Kohler, Temperance, both of Mich.; James A. Ringlien, Maumee, Ohio

[73] Assignee: Owens-Illinois Glass Container Inc., Toledo, Ohio

[21] Appl. No.: 845,740

[22] Filed: Mar. 2, 1992

Related U.S. Application Data

[63] Continuation of Ser. No. 522,767, May 14, 1990, abandoned.

[51] Int. Cl.$^5$ ............................................. G01N 21/90
[52] U.S. Cl. ................................. 356/428; 250/223 B; 356/240
[58] Field of Search ............................... 356/240, 428; 250/223 B

[56] References Cited

U.S. PATENT DOCUMENTS

| | | | |
|---|---|---|---|
| 2,902,151 | 9/1959 | Miles et al. | 356/428 |
| 3,249,224 | 5/1966 | Uhlig . | |
| 3,267,796 | 8/1966 | Mathias | 356/428 |
| 3,386,579 | 6/1968 | Schulze et al. . | |
| 4,213,702 | 7/1980 | Bryant et al. | 250/223 B |
| 4,399,357 | 8/1983 | Dorf et al. . | |
| 4,492,476 | 1/1985 | Miyazawa | 250/223 B |
| 4,584,469 | 4/1986 | Lovalenti | 250/223 B |
| 4,701,612 | 10/1987 | Sturgill | 356/240 |
| 4,731,649 | 3/1988 | Chang et al. . | |
| 4,758,084 | 7/1988 | Tokumi et al. . | |
| 4,807,995 | 2/1989 | Dassler et al. . | |
| 4,958,223 | 9/1990 | Juvinall et al. | 358/106 |

Primary Examiner—Richard A. Rosenberger

[57] ABSTRACT

Apparatus for detecting vertical checks in the finish of a translucent container that includes a light source for directing light energy onto the container finish from externally of the container finish laterally of the container axis over an angular portion less than the entire circumference of the container finish. An area array camera is positioned externally of the container at an angle to the container axis so as to receive an image of the illuminated portion of the container finish. The camera is oriented with respect to the light source such that a vertical check in the container finish reflects light energy from the source to the camera to create a bright a image of the check against a normally dark background. Vertical checks in the container finish are detected as a function of such reflected light energy.

4 Claims, 2 Drawing Sheets

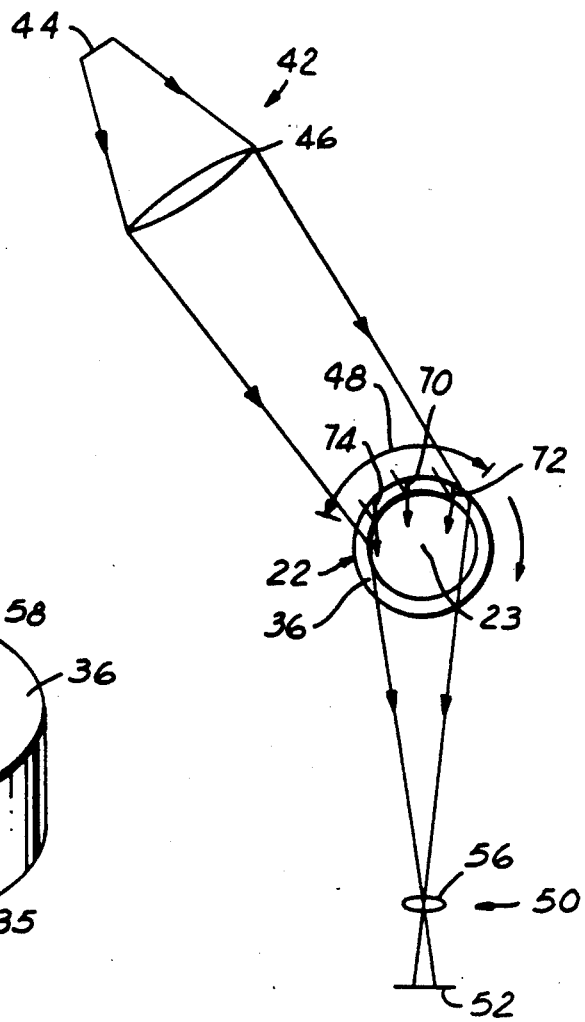
FIG. 2
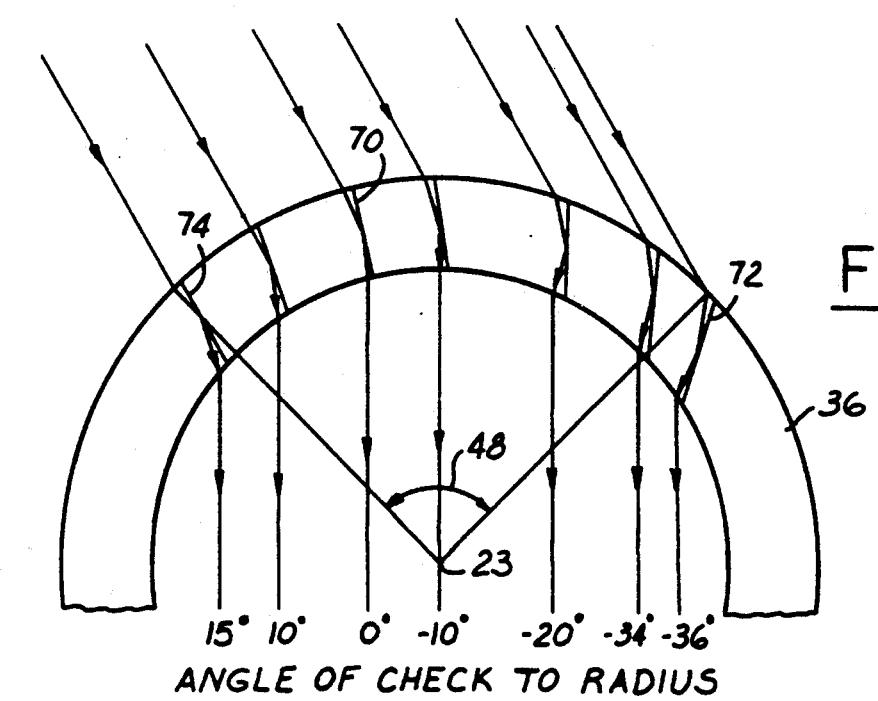
FIG. 3
FIG. 4
ANGLE OF CHECK TO RADIUS

INSPECTION OF CONTAINER FINISH

This is a continuation of application Ser. No. 07/522,767 filed May 14, 1990, now abandoned.

The present invention is directed to optical inspection of translucent containers, and more specifically to an apparatus and method for inspecting the finish of containers for vertical checks.

BACKGROUND AND OBJECTS OF THE INVENTION

In the art of container manufacture, the term "container finish" generally refers to that portion of the container that defines the container mouth. In a bottle, for example, the finish includes that portion of the container neck having threads and/or shoulders for receiving the container cap, as well as the upper surface of the neck surrounding the container mouth against which the cap seats. It is important that the container finish be properly manufactured so that a cap may be affixed thereto to seal the container cavity against leakage and escape of carbonation during handling and storage.

Conventional technology for mass production of glass or plastic containers involves forming the containers in a multiplicity of molds. It has heretofore been proposed to employ optical scanning techniques for inspecting such containers for variations that affect optical characteristics of the container. In U.S. Pat. Nos. 4,378,493, assigned to the assignee of the present application, there are disclosed methods and apparatus in which glass containers are conveyed through a plurality of stations where they are physically and optically inspected. At one inspection station, a glass container is held in vertical orientation and rotated about its vertical axis. An illumination source directs diffused light energy through the container sidewall. A camera, which includes a plurality of light sensitive elements or pixels oriented in a linear array parallel to the vertical axis of container rotation, is positioned to view light transmitted through a vertical strip of the container sidewall. The output of each pixel is sampled at increments of container rotation, and event signals are generated when adjacent pixel signals differ by more than a preselected threshold level. An appropriate reject signal is produced and the rejected container is sorted from the conveyor line.

U.S. Pat. No. 4,584,469 discloses a device for detecting vertical checks in the sidewall of a glass container. A "vertical check" is a minute planar crack that extends into the container wall and is parallel to the container axis. (Directional terms such as "vertical" assume vertical orientation of the container axis with the mouth opening upwardly, as is typical in the container inspection art.) A light source is positioned to one side of the container to direct light energy onto the container wall from a direction perpendicular and lateral to the container axis. An optical detector is positioned to receive an image of the illuminated portion of the container wall from a direction perpendicular to the illumination and container axes. As the container is held in position and rotated about its axis, a planar check will eventually be rotated into a position to reflect light from the source onto the detector. Thus, the vertical check is detected as a bright spot on what is otherwise a normally grey or dark background viewed by the detector.

Two problems are presented by such prior art apparatus for detecting vertical checks in the container sidewall. First, since the light source is tightly focused at the container sidewall and of fairly limited angular extent, light from the source reflected by the check will not be directed onto the detector if the check is other than nearly radially oriented. Second, the detector senses presence of a radially oriented check, but cannot resolve details of the check such as size, and therefore cannot discriminate from other commercial variations that reflect light onto the camera. It is therefore a general object of the present invention to provide a method and apparatus for detecting vertical checks in the finish of translucent containers, such as glass bottles, that include facility for detecting non-radially oriented checks over a wide angular range with respect to the container axis, are capable of resolving size and orientation of the check, distinguishing acceptable commercial variations in finish quality from unacceptable checks, and/or are capable of distinguishing between vertical checks and dust, mold seams or other manufacturing variations.

SUMMARY OF THE INVENTION

The present invention embodies three features that address the deficiencies of the prior art noted above. First, the light source is configured to illuminate a substantial angular portion of the container finish, rather than being focused to a particular point or line at the finish as in the prior art. Thus, as the container is rotated about its axis, a check will be illuminated by the light source for a substantial angular portion of such rotation, and will eventually be brought into a position to reflect light onto the detector even though the check is not radially oriented. Second, the optical detector in accordance with the invention comprises an area matrix detector having a multiplicity of individual light detecting elements disposed in a row and column array. The finish area is imaged by a lens onto the area matrix detector. In this way, by appropriately interrogating the detector array, not only can a vertical check be sensed, but information as to size and orientation can be obtained as a function of the number of array elements that sense reflection from the check. Third, the light source and camera are positioned so that a check is viewed as a bright spot on an otherwise dark (or gray) background. This enhances ability to detect and resolve checks.

Thus, apparatus for detecting vertical checks in the finish of a transparent or colored container includes a light source for directing light energy onto the container finish from externally of the container finish laterally of the container axis over an angular portion less than the entire circumference of the container finish. An area array camera is positioned externally of the container at an angle to the container axis so as to receive an image of the illuminated portion of the container finish. The camera is oriented with respect to the light source such that a vertical check in the container finish reflects light energy from the source to the camera to create a bright image of the check against a normally dark (or grey) background. Vertical checks in the container finish are detected as a function of such reflected light energy.

In the preferred embodiment of the invention, the light source is positioned beneath the plane of the container sealing surface that surrounds the container mouth so as to direct light energy onto the exterior surface of the finish sidewall along an upwardly angulated axis that intersects the container axis of rotation. The camera is positioned above the sealing surface plane so as to receive an image of the illuminated wall portion of the container finish along an image axis that intersects the container axis of rotation and at an angle to the axis of illumination. The illumination and image axes are coplanar.

BRIEF DESCRIPTION OF THE DRAWINGS

The invention, together with additional objects, features and advantages thereof, will be best understood from the following description, the appended claims and the accompanying drawings in which:

FIG. 2 is a fragmentary top plan view of the apparatus in FIG. 1 that illustrates orientation of the light source and camera with respect to the container axis of rotation;

FIG. 3 is a schematic diagram that illustrates image of the container finish at the camera; and FIG. 4 is an enlarged view of a portion of FIG. 2 showing light reflection at various check angles.

DETAILED DESCRIPTION OF PREFERRED EMBODIMENT

Figure 1:
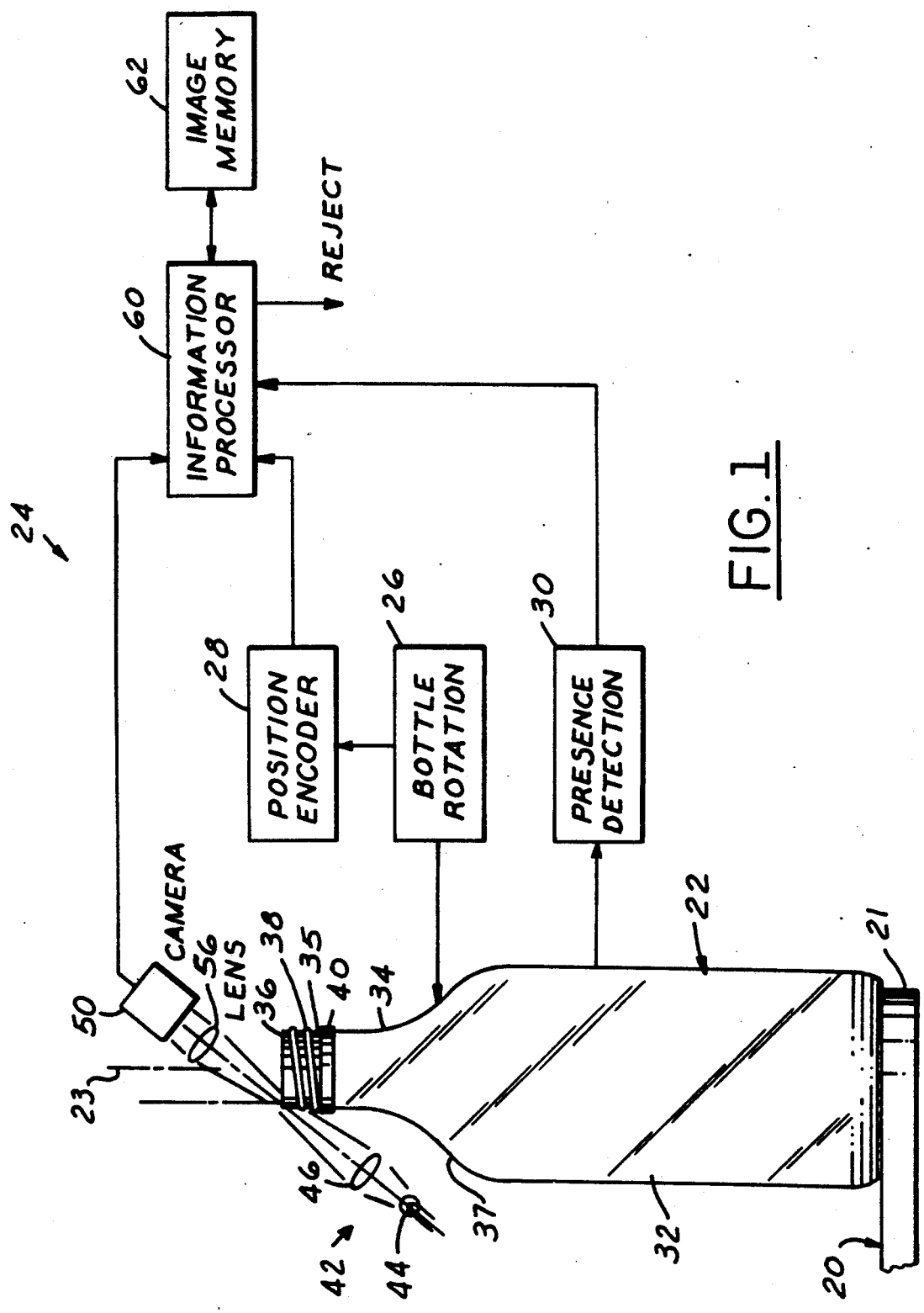
FIG. 1 is a schematic diagram of apparatus for inspecting the finish of containers in accordance with a presently preferred embodiment of the invention.

Referring to FIG. 1, a conveyor 20, typically including a starwheel (not shown) and a slide plate 21, is so disposed and connected to a source of molded containers as to bring successive containers 22 into position at a finish inspection station 24. Conveyor 20 may be of any suitable type, such as those shown in U.S. Pat. Nos. 4,230,219 and 4,378,493, and would typically include a rotatable starwheel for bringing successive containers into position and holding the containers in fixed position during the scanning operation. A bottle rotating device 26, such as a drive roller, is positioned to engage container 22 at station 24 and to rotate the container about its central axis 23. An encoder 28 is coupled to the container rotation mechanism to provide signals indicative of increments of container rotation. A detector 30, such as a switch, is positioned to provide a signal indicative of presence of container 22 at station 24.

In the preferred implementation of the invention herein discussed, container 22 is illustrated as a molded glass bottle having a container body 32 and a generally cylindrical neck 34 that projects upwardly from the body shoulder 37. The finish portion 35 of the container includes an upper portion of neck 34 that terminates in a planar cap surface 36. A helical thread 38 is integrally molded into the outer surface of the finish wall that surrounds the container mouth, and a lip or shoulder 40 is likewise formed on the finish wall outer surface over which a cap skirt may be crimped in the usual manner for affixing the cap to the container. In general, the present invention is disclosed in conjunction with apparatus adapted to detect vertical checks in container finish 35 adjacent and extending downwardly from container sealing surface 36.

A light source 42 is positioned to one side of container finish 35 beneath the plane of sealing surface 36 and is oriented to direct light energy onto the container finish at and beneath the sealing surface along an upward axis that intersects container axis of rotation 23 (as best seen in FIG. 2). Light source 42 includes a lamp 44 and a lens 46 for directing the radiation of lamp 44 at a vertical angle to the container axis and illuminating a substantial angular portion 48 (FIG. 2) less than the entire circumference of the container finish. Preferably, the container finish is illuminated around a circumferential angle of 90°.

A camera 50 includes an area array detector 52 (FIGS. 2 and 3) having a plurality of light sensitive elements 54 disposed in horizontal rows perpendicular to the container axis and vertical columns at an angle to the container axis. An image of illuminated portion 48 of container finish 35 is formed by a lens 56 onto detector array 52 along an optical axis that intersects axis 23 of container 22. Camera 50 views illuminated portion 48 of container finish 34 from above and across the container mouth, receiving an image of container sealing surface 36 and interior finish wall surface 58, as best seen in FIG. 3. The optical axis of camera 50 is at an angle to and coplanar with the illumination axis of light source 42.

An information processor 60 receives signals from detector 30 indicating presence of a container 22 at inspection station 24, and signals from encoder 28 indicative of increments of container rotation. Camera 50 is likewise coupled to information processor 60 for receiving scan control signals, and providing to processor 60 signals indicative of intensity of light incident on the camera from container finish 35 and light source 42. Information processor 60 is connected to an image memory 62, and has an output for providing a reject signal to container sorting apparatus (not shown).

In accordance with an important feature of the present invention illustrated in FIG. 2, a vertical check is illuminated by light source 42 over a substantial angular portion of container rotation, and will eventually be brought into an angular orientation to reflect light energy onto detector array 52 even though the check is not radially oriented. For example, radially oriented vertical check 70 is positioned to reflect light energy from source 42 to camera 50 at about the mid portion of angular range 48. On the other hand, non-radial checks 72,74 are positioned to reflect light energy from source 42 to camera 50 near the ends of illumination angle 48. As best seen in FIG. 4, total angular image of vertical checks is about 50° (−30° to +15° with respect to the container radius) for a total illumination angle 48 of about 90°. Thus, by illuminating a substantial portion of the container finish, as distinguished from focusing the light onto the container finish as in the prior art discussed above, vertical checks may be detected over a substantial angular range with respect to the radius.

Light source 42 may comprise a group of pulsed LEDs or a strobe light. The image of the check will not smear as the bottle rotates between frames because of the strobing action of the light source. A sharp image is obtained and full size information is retained. As described earlier, the check may only reflect light into the camera when it is in the correct angular orientation, therefore frames or images of the bottle will have to be taken in small increments of bottle rotation to make sure that a image is taken of the check when it is in the proper angular orientation. This may have to be about 10° of bottle rotation, or 36 frames to cover the bottle with no overlap.

As an alternative, light source 42 may comprise an incandescent lamp. In this case, the image of the check will smear as the bottle rotates during the frame time. This will reduce the information about the actual size of the check. However, when the check is in the proper angular orientation, the light will be stored in the array. This will happen continuously as the bottle rotates, and not just at the bottle orientations when a strobe fires.

Therefore, fewer frames or images of the bottle would be required. If the camera views 90° of the container finish, then only 4 frames from the camera would be necessary with no overlap. The check would not smear through the full image, but would reflect light only when it is in the proper orientation to reflect light into the camera. This would somewhat limit its apparent smear and would give information as to the angle of the check.

A two-dimensional image of the vertical check is thus received on camera array sensor 52. Sensor 52 is preferably scanned by information processor 60 at increments of container rotation. (This may also be accomplished by scanning the camera array sensor at periodic time increments while rotating the container, thereby eliminating position encoder 28.) U.S. application Ser. No. 448,531, filed Dec. 1, 1989 (16068D), now U.S. Pat. No. 4,958,113, discloses a container inspection device and method in which the camera includes an area array sensor having a first transport register for receiving image data from corresponding rows of image sensing elements 54 (FIG. 3), a second transport register for receiving image data from the first transport registers by element column, and an output amplifier for selectively transmitting image data from the second transport register. Information processor 60 includes facility for selectively integrating image data from adjacent columns of sensing elements at the second transport register, and for selectively integrating image data from adjacent rows of sensing elements at the output amplifier. In accordance with such disclosure, a reduced amount of data is collected from the camera and analyzed by the information processor. This results in reduced memory requirements, increased speed and improved signal-to-noise ratio. The technique disclosed in such copending application, which is incorporated herein by reference, may be employed to advantage in the apparatus and method of the present invention.

We claim:

1. Apparatus for detecting vertical checks in the finish of a translucent container having a central axis and an open mouth comprising:

means for rotating the container about its central axis, a source for directing light energy onto the finish of the container as it rotates from externally of the container laterally of the container axis over an angular portion of substantially 90° of the container finish, a camera that includes an area array sensor containing a matrix of image sensing elements arranged in a row-and-column array positioned externally of the container at an angle to the container axis and means for directing onto said array an image of the illuminated portion of the container finish as the container rotates, said camera being oriented with respect to said light source such that a vertical check in the container finish reflects light energy from the source to the camera as the check passes through that portion of the container finish that is illuminated to create a bright image of the check against a normally dark background, and means responsive to said camera for detecting vertical checks in the container finish as a function of such reflected light energy, said camera-responsive means including information processing means coupled to said camera for scanning said element array at increments of container rotation and obtaining a two-dimensional image of vertical checks at the container finish at each said increment of container rotation, said information processing means including electronic memory and means for storing in said memory each said two-dimensional image of vertical checks detected at the container finish at successive increments of container rotation.

2. The apparatus set forth in claim 1 wherein said source includes means positioning said source on one axial side of said mouth so as to direct light energy onto said finish along an axis that intersects the container axis, and wherein said camera includes means positioning said camera on an axial side of said mouth opposed to said source to receive said image along an axis that intersects the container axis and at an angle to said axis of illumination.

3. The apparatus set forth in claim 2 wherein said illumination and image axes are coplanar.

4. A method of detecting vertical checks in the finish of a translucent container comprising the steps of:

rotating the container about is central axis, directing light energy onto one sidewall of the container finish from externally of the container laterally of the container axis over an angular portion of substantially 90° of the container finish, directing an image of the illuminated wall portion of the container finish onto an array sensor positioned on a laterally opposed side of the said wall portion from said light source, orienting said sensor with respect to said light source such that a vertical check in the container finish as the container rotates to create a bright image of the check against a normally dark background, scanning said sensor at increment increments of container rotation to develop a two-dimensional image at each scan increment of any vertical checks in the illuminated portion of the container finish, and detecting vertical checks in the container as a function of such two-dimensional image.

* * * * *